United States Patent
Szewczyk et al.

(10) Patent No.: US 9,750,825 B2
(45) Date of Patent: *Sep. 5, 2017

(54) MULTIPHASE ORAL CARE COMPOSITIONS

(75) Inventors: Gregory Szewczyk, Flemington, NJ (US); Neeta Atul Patel, Monmouth Junction, NJ (US); Suzanne Jogun, Wayne, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/365,113

(22) PCT Filed: Dec. 16, 2011

(86) PCT No.: PCT/US2011/065309
§ 371 (c)(1),
(2), (4) Date: Jun. 13, 2014

(87) PCT Pub. No.: WO2013/089760
PCT Pub. Date: Jun. 20, 2013

(65) Prior Publication Data
US 2014/0341816 A1 Nov. 20, 2014

(51) Int. Cl.
*A61Q 11/00* (2006.01)
*B65D 35/00* (2006.01)
*A61K 8/02* (2006.01)
*A61K 8/73* (2006.01)
*A61K 8/34* (2006.01)
*A61K 8/49* (2006.01)
*A61K 49/00* (2006.01)

(52) U.S. Cl.
CPC ............ *A61K 49/00* (2013.01); *A61K 8/0204* (2013.01); *A61K 8/0233* (2013.01); *A61K 8/345* (2013.01); *A61K 8/4993* (2013.01); *A61K 8/731* (2013.01); *A61K 8/732* (2013.01); *A61Q 11/00* (2013.01); *B65D 35/00* (2013.01); *A61K 2800/43* (2013.01)

(58) Field of Classification Search
CPC ...... A61K 8/345; A61K 8/4993; A61K 8/731; A61K 8/0233; A61K 8/0204; A61K 8/732; A61K 49/00; A61K 2800/00; A61Q 11/00; B65D 39/00
See application file for complete search history.

(56) References Cited

U.S. PATENT DOCUMENTS

| | | | |
|---|---|---|---|
| 3,662,059 A | 5/1972 | Wiesner et al. | |
| 4,969,767 A | 11/1990 | Madden | |
| 5,020,694 A | 6/1991 | Pettengill | |
| 6,136,297 A | 10/2000 | Sagel et al. | |
| 6,479,036 B1 | 11/2002 | Stanier et al. | |
| 6,669,229 B2 | 12/2003 | Thomas | |
| 7,763,235 B2 | 7/2010 | Boyd et al. | |
| 2002/0034479 A1 | 3/2002 | Green | |
| 2004/0247646 A1 | 12/2004 | Ivory et al. | |
| 2005/0019273 A1 | 1/2005 | Boyd et al. | |
| 2006/0134020 A1 | 6/2006 | Robinson et al. | |
| 2007/0020201 A1 | 1/2007 | Boyd et al. | |
| 2007/0148213 A1 | 6/2007 | Ibrahim et al. | |
| 2008/0138369 A1 | 6/2008 | Boyd et al. | |
| 2008/0187497 A1* | 8/2008 | Agarwal ............... | A61K 8/0237 424/49 |
| 2008/0187498 A1* | 8/2008 | Francis ................... | A61K 8/02 424/49 |
| 2008/0245678 A1 | 10/2008 | Gantenberg | |
| 2008/0247967 A1 | 10/2008 | Sagel | |
| 2008/0247968 A1 | 10/2008 | Sagel | |
| 2008/0247969 A1 | 10/2008 | Glandorf | |
| 2008/0247970 A1 | 10/2008 | Gantenberg | |
| 2008/0248072 A1 | 10/2008 | Glandorf | |
| 2008/0248073 A1 | 10/2008 | Gantenberg | |
| 2008/0260836 A1 | 10/2008 | Boyd | |
| 2009/0060597 A1 | 3/2009 | Yoshida et al. | |
| 2009/0317432 A1* | 12/2009 | Kergosien ............... | A61K 8/02 424/401 |

FOREIGN PATENT DOCUMENTS

| | | |
|---|---|---|
| CN | 1756524 | 4/2006 |
| CN | 101111216 | 1/2008 |
| EP | 0255210 | 2/1988 |
| EP | 1843738 | 10/2007 |
| EP | 2105122 | 9/2009 |
| EP | 2116219 | 11/2009 |
| JP | S61-271214 | 12/1986 |
| JP | H10-265355 | 10/1998 |
| JP | 2005-075756 A | 3/2005 |
| RU | 2417621 | 5/2011 |
| TW | 200819149 | 5/2008 |
| WO | WO 9317935 * | 9/1993 |

(Continued)

OTHER PUBLICATIONS

Boff et al. (WO 2005058265 A1, English Translation), 2005.*
Eng. Translation for CN1756524 B, Oral Care Compositions and methds—Apr. 2006; Google Translated.*
International Search Report and the Written Opinion issued in International Application PCT/US2011/65309 mailed Sep. 28, 2012. WO.
Written Opinion of the International Preliminary Examining Authority issued in International Application PCT/US2011/65309 mailed Jan. 22, 2014. WO.

*Primary Examiner* — Blessing M Fubara

(57) ABSTRACT

Described herein are dentifrices comprising a first formulation and a second formulation, wherein the formulations are coaxially extruded, so that the first formulation enrobes the second formulation, wherein the first formulation is opaque and wherein the second formulation comprises dissolvable film fragments, together with methods of making and using the same and containers for providing the same.

12 Claims, No Drawings

(56) References Cited

FOREIGN PATENT DOCUMENTS

| WO | WO9317935 | 9/1993 |
| WO | WO 99/01342 | 1/1999 |
| WO | WO 99/01342 A1 * | 1/1999 |
| WO | WO 2005/037240 | 4/2005 |
| WO | WO2006081924 | 8/2006 |
| WO | WO 2008/008617 | 1/2008 |
| WO | WO 2010/053492 | 5/2010 |
| WO | WO 2010/114551 A1 * | 10/2010 |
| WO | WO2010114551 | 10/2010 |

* cited by examiner

MULTIPHASE ORAL CARE COMPOSITIONS

CROSS-REFERENCE TO RELATED PATENT APPLICATIONS

The present application is a U.S. national stage entry under 35 U.S.C. §371 of Patent Cooperation Treaty Patent Application No. PCT/US2011/65309, filed Dec. 16, 2011, the entirety of which is incorporated herein by reference.

BACKGROUND

It is recommended that children should brush their teeth for at least 45-60 seconds, and adults for at least 90 to 120 seconds. Most people, especially children, do not brush their teeth for a sufficient period of time to obtain maximum benefit, and moreover have difficulty accurately estimating the time necessary to brush the teeth.

There is a need for improved, consumer-friendly products and methods to encourage users to brush their teeth for the appropriate period of time.

SUMMARY

We decided to make a toothpaste comprising film fragments or capsules comprising a high concentration pigment, which would be stable in formulation, but would break down and provide a color change after a sufficient period of brushing. The user would be instructed to continue brushing until the color change was observed, so as to help ensure that the user brushed for a sufficient period of time. We found one problem with this approach, however, is that particles containing very high concentrations of pigment tend to appear black, so that a toothpaste comprising such films or capsules would appear to have flecks of dirt or ash, which would be unattractive to consumers. In other aspects, it would be desirable to reduce the visibility of the pigment-containing film fragments so as to create an element of surprise when brushing is sufficient to disintegrate the film fragments and release the pigment.

In a first attempt to overcome this problem, we made white-black-white triple layer films. The white outer layer comprised titanium dioxide, an opaque white pigment, which concealed the middle layer which looks black, due to high pigment loading, by the outer white layers. While these film fragments were more aesthetically appealing in formulation than the black fragments, the triple layer films turned out to be much more expensive to make than the single layer black films. Moreover, in gel formulations, the large amounts of titanium dioxide pigment tended to obscure the color change signal from the darker pigment, so that the color change signal was less noticeable. Finally, if different colors that white were desired, they would have to be made in different film batches, which would further add to the expense.

The problem presented, which was not obvious at the outset of the project, was to find a simple and inexpensive way to enhance the visual aesthetics of the dentifrice without compromising the functionality of the film to provide a noticeable color change after sufficient brushing.

A new method for enhancing stability of the film fragments as well as enhancing the visual aesthetics of the product is co-extruding two dentifrice formulations coaxially, i.e., with one formulation wrapped cylindrically around the other. While "enrobing" or coaxial extruding with a clear outer gel layer and an opaque inner core has sometimes been used to draw attention to different phases, the use of coaxial extrusion to hide films at the core is new and highly effective.

Some embodiments of the present invention utilize enrobing in a unique way where two opaque phases are used so as to not draw any attention to the fact that more than one layer exists. The separation does not in any way inhibit color generation during brushing, where formulations provide a definite signal by 100 seconds of brushing. A further advantage of the formulations is enhanced stability. The films themselves are often degraded by components of the dentifrice and therefore the paste must be formulated to avoid use of components that could degrade the films during storage. In some embodiments, the present invention permits segregation of the films into a more stable environment.

Some embodiments of the present invention thus provide a dentifrice product comprising a first formulation and a second formulation, wherein the formulations are coaxially extruded, so that the first formulation enrobes the second formulation, wherein the first formulation is opaque and wherein the second formulation comprises dissolvable film fragments, e.g. film fragments comprising a pigment, wherein the film fragments disintegrate during use of the dentifrice and the pigment released thereby changes the color of the dentifrice, e.g., to signal to the user that brushing has continued for an adequate period of time. The invention further provides methods of cleaning the teeth comprising brushing with such a dentifrice until the pigment is released. In yet another embodiment, the invention provides a novel process for making a dentifrice comprising axially coextruding a first formulation which enrobes a second formulation, wherein the first formulation is opaque and wherein the second formulation comprises dissolvable film fragments.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention thus provides, in a first embodiment, a dentifrice product (Dentifrice 1) comprising a first formulation and a second formulation, wherein the formulations are coaxially extruded, so that the first formulation enrobes the second formulation, wherein the first formulation is opaque and wherein the second formulation comprises dissolvable film fragments; for example, 1.1. Dentifrice 1 wherein the film fragments are stable in the formulation but disintegrate during use of the dentifrice;
1.2. Dentifrice 1 or 1.1 wherein the film fragments comprise a pigment that is released upon disintegration of the film fragments during use of the dentifrice;
1.3. Any of the foregoing dentifrices wherein the film fragments comprise cellulose ethers, e.g., selected from
    (i) alkylcellulose, e.g., methylcellulose;
    (ii) hydroxyalkyl cellulose, e.g., selected from hydroxypropyl methyl cellulose, hydroxyethylpropyl cellulose, hydroxybutyl methyl cellulose, hydroxy propyl methyl cellulose, carboxymethyl cellulose and mixtures thereof;
and (iii) mixtures thereof;

1.4. Any of the foregoing dentifrices wherein the film fragments comprise a starch, e.g. a pregelatinized starch;

1.5. Any of the foregoing dentifrices wherein the film fragments comprise a plasticizer, e.g, a polyalcohol, e.g., sorbitol, propylene glycol, glycerol, or low molecular weight polyethylene glycol, e.g., PEG 200;

1.6. Any of the foregoing dentifrices wherein the film fragments comprise propylene glycol, e.g., in an amount effective to provide plasticity to the film, e.g., about 20-30% by dry weight of the film;

1.7. Any of the foregoing dentifrices wherein the film fragments comprise a non-ionic surfactant or emulsifier, e.g., a polysorbate, e.g., polysorbate 80 (also known as polyoxyethylene(20) sorbitan monooleate, available commercially e.g., as Tween® 80), e.g., in an amount of about 1-5% by dry weight of the film;

1.8. Any of the foregoing dentifrices wherein the film fragments comprise a pigment, e.g., a red pigment, for example D&C Red 30, a green pigment, for example Pigment Green 7, a blue pigment, for example a phthalocyanine, for example Pigment Blue 15, or a combination of any of these pigments.

1.9. Any of the foregoing dentifrices wherein the film fragments are substantially dissolved after a period of greater than 30 seconds and less than 180 seconds of brushing in the presence of water; e.g., after brushing for about 45-60 seconds in a dentifrice for use by a child and about 90-120 seconds in a dentifrice for use by an adult, thereby releasing a pigment contained in the film fragments and providing a color signal to the user of adequate brushing;

1.10. Any of the foregoing dentifrices wherein the average thickness of the film fragments is 0.5-5 mil, e.g., about 1.5-3 mil;

1.11. Any of the foregoing dentifrices wherein the film fragments comprise by dry weight of the film, (i) 20-60% cellulose ethers selected from methyl cellulose, hydroxypropylmethyl cellulose, and mixtures thereof, (ii) 10-30% propylene glycol; 1-5% polysorbate 80, and 15-55% pigment;

1.12. Any of the foregoing dentifrices wherein the film fragments disintegrate following at least 30 seconds and not more than about 180 seconds, e.g., about 45-60 seconds in a toothpaste for use by a child and about 90-120 seconds in a toothpaste for use by an adult, thereby releasing the pigment and providing a color signal to the user of adequate brushing;

1.13. Any of the foregoing dentifrices optionally further comprising one or more of one or more of water, abrasives, surfactants, foaming agents, vitamins, polymers, enzymes, humectants, thickeners, antimicrobial agents, preservatives, flavorings, colorings and/or combinations thereof;

1.14. Any of the foregoing dentifrices wherein the water activity of the first formulation is higher than the water activity of the second formulation, e.g. wherein the first formulation has a water activity greater than 0.75 and the second formulation has a water activity less than 0.75.

In some embodiments, the pigment contained in the film fragments is substantially released at a specific point in time, and does not slowly leak from the film or film fragments. In some embodiments, the terms "film" and "film fragments" are used interchangeably.

In some embodiments, substantially all of the pigment is released from the film at one time. As used herein, the term "substantially all" refers to greater than 90% of the total amount of pigment contained in the film. In some embodiments, the film releases at least 90% of the total amount of pigment contained therein, at a particular point in time. In some embodiments, the film releases greater than 90% of the total amount of pigment contained therein, at a designated point in time. In some embodiments, the film releases at least 91% of the total amount of pigment contained therein, at the designated point in time. In some embodiments, the film releases at least 95% of the total amount of pigment contained therein, at the designated point in time. In some embodiments, the film releases at least 96% of the total amount of pigment contained therein, at the designated point in time. In some embodiments, the film releases at least 97% of the total amount of pigment contained therein, at the designated point in time. In some embodiments, the film releases at least 98% of the total amount of pigment contained therein, at the designated point in time. In some embodiments, the film releases at least 99% of the total amount of pigment contained therein, at the designated point in time.

In some embodiments, the first formulation and second formulation both comprise film fragments. In some embodiments, only one of the first and second formulations comprises film fragments.

The invention further provides a toothpaste container capable of co-axial extrusion of a first dentifrice formulation which is opaque and a second dentifrice formulation which comprises film fragments, such that upon extrusion, the first formulation enrobes the second formulation; for example, a toothpaste container having an aperture, a first zone or compartment within the container containing a first flowable dentifrice formulation which is opaque, and a second zone or compartment within the container containing a second flowable dentifrice formulation comprising dissolvable film fragments, wherein the aperture is adapted for coaxial extrusion and has an outer opening in fluid communication with the first zone or compartment, said outer opening being coaxially oriented around a central opening in fluid communication with the second zone or compartment, and wherein the volume of the first and second zones or compartments can be reduced, e.g., by compression of the container or depression of a plunger attached to the container, such that when the volume of first and second zones or compartments is reduced, the first and second formulations are coaxially extruded from the aperture, with the first formulation enrobing the second formulation.

The invention further provides a method of cleaning the teeth comprising brushing with a dentifrice, e.g, any of Dentifrice 1 et seq., as described in above, wherein the film fragments comprise a pigment and brushing is continued until the film fragments dissolve and the pigment provides a color signal to the user of adequate brushing, for example, when the brushing time before the film fragments dissolve is between 30 and 180 seconds, e.g., about 45-60 seconds for a toothpaste for use by a child and about 90-120 seconds for a toothpaste for use by an adult.

The invention further provides a method of making a dentifrice, e.g., a dentifrice according to any of Dentifrice 1 et seq. described above, comprising coaxially extruding a first formulation and a second formulation, so that the first formulation enrobes the second formulation, wherein the first formulation is opaque and wherein the second formulation comprises dissolvable film fragments.

The compositions of the invention are intended for topical use in the mouth, thus components for use in the present invention should be orally acceptable, that is, safe for topical use in the mouth, in the amounts and concentrations provided.

Toothpaste containers for co-extrusion of two or more formulations are known in the art. See, e.g. U.S. Pat. Nos. 5,020,694; 4,969,767.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight.

EXAMPLES

Example 1

Pigment is incorporated into films to trigger color change during brushing. Single layer films are less expensive to make but not attractive to some consumers, as the high pigment load makes them appear black. Triple layer white-black-white films are made to hide the black films to make white films, which are more attractive, but these triple films are very expensive. Moreover, the formulation options are constrained by the requirement to avoid formulations in which the film will be unstable. The challenge therefore is to make a dentifrice formulation which changes color during brushing to signal a minimum period of brushing, which is economical to make, which is visually appealing, and which provides a stable environment for pigment-containing film fragments during storage.

A prototype color change toothpaste product is developed by encapsulating the pigment into a dissolvable polymer film. During brushing, the films swell from water and disintegrate, releasing the pigment and, thus, color change occurs to indicate the consumer when the brushing is done. The goal is to use color change signal to increase the brushing time for the consumer by controlling the brushing time at 45-60 sec for children and 90-120 sec for the adults.

Two film options are developed: (1) single layer black films which are less expensive and have very strong color change signal (high color change contrast), (2) triple layer white-black-white films which hide the black film in the middle. These triple layer films are more consumer-acceptable visually, however in gel formulations, the color change contrast is diminished due to the high color-covering power of TiO2 from the outer layers, and the triple layer films are in any event expensive to make.

A prototype film is made making a slurry in water using the following ingredients then drying to obtain a film having an average thickness of about 2 mil:

TABLE 1

| Ingredient | Weight % of solids |
|---|---|
| Hydroxypropylmethyl cellulose | 6 |
| Methylcellulose | 41 |
| Pigment (Blue 15) | 30 |
| Propylene Glycol | 21 |
| Polysorbate (Tween 80) | 2 |
| Total | 100 |

In some embodiments film fragments are mixed into a low water toothpaste gel base (Formula 2/Table 2), which is enrobed by an opaque paste (Formula 1/Table2). In a second embodiment the film fragments are mixed into a low water opaque toothpaste (formula 3/Table2) which is enrobed by an opaque toothpaste (formula 1/Table2).

The enrobing in laboratory to provide test prototypes is carried out in the following fashion. The outer layer material is filled into a standard tube and the inner layer is filled into a secondary tube with a diameter less than the first tube. The secondary tube is then inserted into the first tube displacing the outer layer toothpaste in a volume equal to the inserted tube. A plunger is applied to the secondary tube and its contents as the secondary tube is slowly removed. The secondary tubes' contents are left behind, enrobed within the primary tubes' contents. The inner core is indistinguishable from the outer core in the case of the opaque pastes. For commercial production, the toothpaste can be dispensed from a tube adapted to provide coaxial extrusion.

TABLE 2

| Ingredients | Formula 1 | Formula 2 | Formula 3 |
|---|---|---|---|
| Water | 5 | 7.6 | 5 |
| Sodium Fluoride | 0.24 | 0.22 | 0.24 |
| Sodium Saccharin | 0.3 | 0.35 | 0.3 |
| Glycerin | 37 | — | 37 |
| Sodium CMC | 1.1 | 0.50 | 1.1 |
| Iota Carrageenan | 0.5 | — | 0.5 |
| Sorbitol | 18 | 71.9 | 18 |
| Propylene glycol | 0.5 | — | 0.5 |
| Gantrez Soln. (16.5%) | 11.82 | — | 11.82 |
| NaOH, 50% Soln. | 1.2 | — | 1.2 |
| Titanium dioxide | 0.75 | — | 0.75 |
| Silica | 21.5 | 8 | 21.5 |
| SLS | 1.5 | 0.5 | 1.5 |
| Film | — | 0.3 | 0.3 |
| Triclosan | 0.3 | — | 0.3 |
| Flavor | 1 | 1 | 1 |

Stability of the film fragments is measured using standard accelerating conditions pursuant to guidelines from International Conference on Harmonization (ICH), and evaluating the change in color after a specified timepoint. The change in color is measured via a colorimetric evaluation of the L*a*b* space with focus on the change in b (Table 3). A baseline of the enrobed formula is first obtained prior to the stability study and measurements are then taken at specified intervals from that generating a delta b (db*) reading. The greater the change in b is indicative of a bluing of the formulation and hence an instability. The change in b as listed in Table 3 demonstrates that when films are segregated into a lower water formula even if there a second phase in contact with the first, no meaningful degradation of films is observed. Dissolution of films, if present, would exhibit db* levels similar to that listed in Table 3 for non-enrobed formulations.

TABLE 3

| | db* (D65) |
|---|---|
| Enrobed Baseline | — |
| Enrobed 2 months 25° C. | −0.04 |
| Enrobed 2 months 40° C. | −0.79 |
| Non-Enrobed | −25.84 |

Example 2

A prototype film is developed by encapsulating a pigment into a dissolvable polymer film. During brushing, the films swell from water and disintegrate, releasing the pigment and, thus, color change occurs to indicate the consumer when the brushing is done. One use for this film is for incorporation into a clear gel or opaque toothpaste providing a color change signal to the consumer after a predetermined brushing time, e.g., 45-60 sec for children and 90-120 sec for the adults.

The ingredients for the prototype film are set forth in Table 4:

TABLE 4

| Ingredient | Weight % of solids |
|---|---|
| Hydroxypropyl methyl cellulose (Methocel E5) | 7 |
| Methyl cellulose (Methocel A15) | 46.5 |
| Pigment (Vibracolor Blue PBL15) | 19.5 |
| Propylene Glycol | 25 |
| Tween 80 | 2 |
| Total Amount | 100 |

The prototype film is made in different thicknesses, and flakes of the prototype film are incorporated into a clear gel toothpaste for testing. A dissolution test in vitro is performed by permitting a 1"×1" swatch of bulk film to float on a container filled with 1 L of tap water at room temperature. The effect on film dissolution caused by changes in thickness can be observed and measured over a period of time. As seen on Table 5, the time before pigment release is seen to be approximately proportional to the thickness of the film:

TABLE 5

Dissolution Test
Blue Pigment - A15

| Avg. Film Thickness (mil) | Weight (g) | Density (g/in3) | First hint of color (sec) | First tear of film (sec) | Dissolution time (sec) |
|---|---|---|---|---|---|
| 1.017 | 0.0156 | 15.3442 | 45 | 50 | 110 |
| 1.683 | 0.0306 | 18.1786 | 95 | 155 | 360 |
| 2.683 | 0.0466 | 17.3686 | 137 | 450 | 1055 |
| 3.000 | 0.0621 | 20.7000 | 126 | 805 | 1295 |

Toothpaste comprising flakes of 1.5 mil in thickness and toothpaste comprising flakes of 3 mil in thickness are then tested side by side in a clinical trial. Dissolution occurs more quickly with actual brushing in the mouth compared to the in vitro test, which does not involve brushing, but the correlation between thickness and release time is maintained.

TABLE 6

| Trial | Dissolution time 1.5 mil first color (seconds) | Dissolution time 3.0 mil first color (seconds) | Dissolution time 1.5 mil max color (seconds) | Dissolution time 3.0 mil max color (seconds) |
|---|---|---|---|---|
| 1 | 26 | 45 | 57 | 105 |
| 2 | 30 | 60 | 25 | 45 |
| 3 | 30 | 35 | 35 | 45 |
| 4 | 60 | 120 | 120 | 180 |
| 5 | 76 | 133 | 126 | 120 |
| 6 | 18 | 71 | 37 | 110 |
| 7 | 10 | 30 | 25 | 60 |
| 8 | 20 | 40 | 28 | 50 |
| 9 | 35 | 60 | 45 | 90 |
| Avg | 33.89 | 66.00 | 55.33 | 89.44 |

The release profile of the 1.5 mil film is within the target for use in a children's toothpaste, whereas the release profile for the 3 mil matches the target for use in an adult toothpaste.

The invention claimed is:

1. A dentifrice comprising a first formulation and a second formulation, wherein the formulations are coaxially extruded, so that the first formulation enrobes the second formulation, wherein the first formulation is opaque and wherein the second formulation comprises dissolvable film fragments;
   wherein the film fragments are stable in the formulation but disintegrate during use of the dentifrice and wherein the film fragments comprise a pigment that is released upon disintegration of the film fragments during use of the dentifrice;
   and wherein the film fragments comprise by dry weight of the film, 20-60% cellulose ethers, 10-30% propylene glycol, 1-5% polysorbate 80, and 15-55% pigment; and wherein the film fragments are single layer film fragments.

2. The dentifrice of claim 1 wherein the cellulose ether is selected from the group consisting of an alkylcellulose, a hydroxyalkyl cellulose, and a combination of two or more thereof.

3. The dentifrice of claim 1 wherein the film fragments further comprise a starch.

4. The dentifrice of claim 1 wherein the film fragments are substantially dissolved after a period of greater than 30 seconds and less than 180 seconds of brushing in the presence of water, thereby providing a color signal to the user of adequate brushing.

5. The dentifrice of claim 1 wherein the average thickness of the film fragments is 0.5-5 mils.

6. The dentifrice of claim 1 wherein the cellulose ethers are selected from the group consisting of methyl cellulose, hydroxypropylmethyl cellulose, and mixtures thereof.

7. The dentifrice of claim 1 further comprising one or more of water, abrasives, surfactants, foaming agents, vitamins, polymers, enzymes, humectants, thickeners, antimicrobial agents, preservatives, flavorings, colorings and/or combinations thereof.

8. The dentifrice of claim 1 wherein the first formulation has a water activity higher than the water activity of the second formulation.

9. A dentifrice comprising a first formulation and a second formulation, wherein the formulations are coaxially extruded, so that the first formulation enrobes the second formulation, wherein the first formulation comprises dissolvable film fragments and the second formulation is opaque.

10. A toothpaste container capable of co-axial extrusion of a first dentifrice formulation which is opaque and a second dentifrice formulation which comprises film fragments, such that upon extrusion, the first formulation enrobes the second formulation, to provide a dentifrice according to claim 1, the toothpaste container having
- an aperture,
- a first zone or compartment within the container containing the first dentifrice formulation, and
- a second zone or compartment within the container containing the second dentifrice formulation,
- wherein the aperture is adapted for coaxial extrusion and has an outer opening in fluid communication with the first zone or compartment, said outer opening being coaxially oriented around a central opening in fluid communication with the second zone or compartment, and
- wherein the volume of the first and second zones or compartments can be reduced,
- such that when the volume of first and second zones or compartments is reduced, the first and second formulations are coaxially extruded from the aperture.

11. A method of cleaning the teeth comprising brushing with a dentifrice according to claim 1 wherein the film fragments comprise a pigment and brushing is continued until the film fragments dissolve and the pigment provides a color signal to the user of adequate brushing.

12. A method of making a dentifrice according to claim 1 comprising coaxially extruding a first formulation and a second formulation, so that the first formulation enrobes the second formulation.

* * * * *